United States Patent [19]

Bargiotti et al.

[11] Patent Number: 4,987,126

[45] Date of Patent: Jan. 22, 1991

[54] 3'-DEAMINO-4'-DEOXY-4'-AMINO ANTHRACYCLINES

[75] Inventors: Alberto Bargiotti; Antonino Suarato; Pierangelo Zini; Maria Grandi; Gabriella Pezzoni, all of Milan, Italy

[73] Assignee: Farmitalia Carlo Erba S.R.L., Milan, Italy

[21] Appl. No.: 308,449

[22] Filed: Feb. 10, 1989

[30] Foreign Application Priority Data

Feb. 10, 1988 [GB] United Kingdom ................. 8803076

[51] Int. Cl.$^5$ ....................... A61K 31/70; C07H 15/24
[52] U.S. Cl. ......................................... 514/34; 536/6.4
[58] Field of Search ............................ 514/34; 536/6.4

[56] References Cited

U.S. PATENT DOCUMENTS

| | | | |
|---|---|---|---|
| 4,067,969 | 1/1978 | Penco et al. | 514/34 |
| 4,112,076 | 9/1978 | Arcamone et al. | 536/6.4 |
| 4,366,149 | 12/1982 | Bargiotti et al. | 514/34 |
| 4,563,444 | 1/1986 | Angelucci et al. | 536/6.4 |

OTHER PUBLICATIONS

Biomedical and Environmental Mass Spectrometry, vol. 13, No. 7, 1986, pp. 319–326, John Wiley & Sons Ltd., C. Monneret et al.: "Desorption Chemical Ionization Mass Spectrometry of Anthracyclines and of Trisaccharides . . . Marcellomycin".

Primary Examiner—Johnnie R. Brown
Assistant Examiner—Elli Peselev

Attorney, Agent, or Firm—Oblon, Spivak, McClelland, Maier & Neustadt

[57] ABSTRACT

Anthracycline glycoside compounds of general formula I or II:

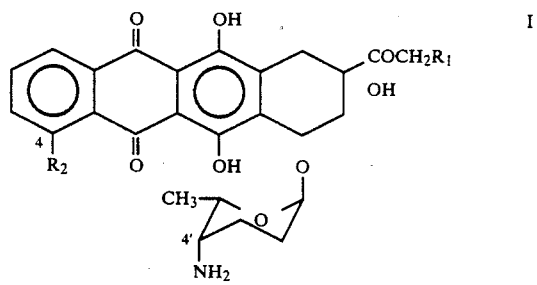

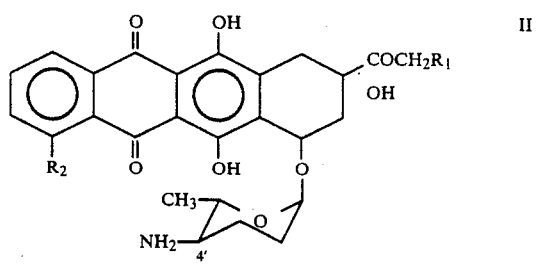

wherein $R_1$ is hydrogen or a hydroxy group and $R_2$ is hydrogen or a methoxy group, and their pharmaceutically acceptable acid addition salts, are antitumor agents.

10 Claims, No Drawings

3'-DEAMINO-4'-DEOXY-4'-AMINO ANTHRACYCLINES

The present invention relates to anthracycline antitumor glycosides, their preparation, compositions containing them and the use of the glycosides.

Daunorubicin (daunomycin), 4-demethoxydaunorubicin and their hydroxylated side chain derivatives are well-known antitumor glycosides, and both their preparation and use are amply described in the prior art. Daunomycinone and 4-demethoxydaunomycinone, which are the aglycones used as starting materials, are also well-known.

The present invention provides, in one aspect thereof, a new class of anthracycline glycosides of the formulae I and II:

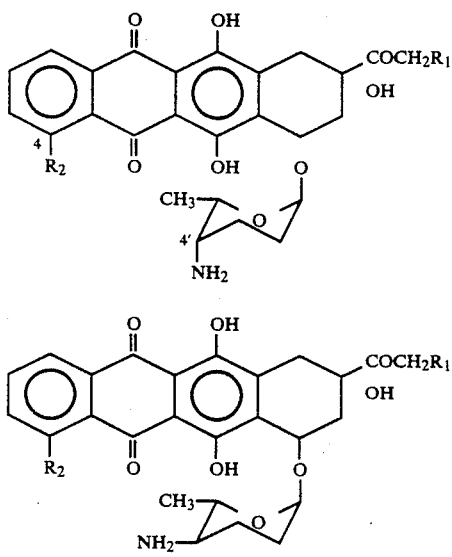

wherein $R_1$ is hydrogen or a hydroxy group and $R_2$ is hydrogen or a methoxy group, and their pharmaceutically acceptable addition salts. A preferred such salt is the hydrochloride. More particularly the new anthracycline glycosides are:

Ia: 4-demethoxy-3'-deamino-4'-deoxy-4'-aminodaunorubicin

Ib: 3'-deamino-4'-deoxy-4'-aminodaunorubicin

Ic: 4-demethoxy-3'-deamino-4'-deoxy-4'-aminodoxorubicin

Id: 3'-deamino-4'-deoxy-4'-aminodoxorubicin

IIa: 4-demethoxy-3'-deamino-4'-deoxy-4'-epi-aminodaunorubicin

IIb: 3'-deamino-4'-deoxy-4'-epi-aminodaunorubicin

IIc: 4-demethoxy-3'-deamino-4'-deoxy-4'-epi-aminodoxorubicin

IId: 3'-deamino-4'-deoxy-4'-epi-aminodoxorubicin

Compounds Ia-d or IIa-d and pharmaceutically acceptable salts thereof are prepared by a process comprising:

(i) condensing daunomycinone or 4-demethoxydaunomycinone or with a compound of formula IIIe or f:

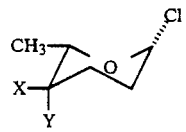

IIIe: X = H  Y = NHCOCF$_3$
IIIf: X = NHCOCF$_3$  Y = H to give the N-trifluoroacetyl glycoside of formula IVe or IVf

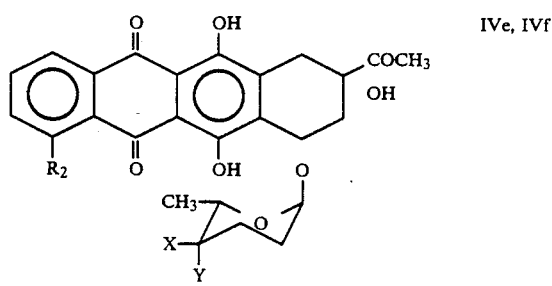

$R_2$ = H or OCH$_3$
e: X = H  Y = NHCOCF$_3$
f: X = NHCOCF$_3$  Y = H and removing the N-trifluoroacetyl group therefrom to obtain an anthracycline glycoside of formula I and II in which $R_1$ is hydrogen and $R_2$ is as defined above:

(ii) if desired, converting the said anthracycline glycoside of formula I or II into a pharmaceutically acceptable salt thereof;

(iii) if desired, brominating the said anthracycline glycoside of formula I or II or pharmaceutically acceptable salt thereof and hydrolyzing the 14-bromo derivative thus obtained to obtain the corresponding anthracycline glycoside of formula I or II in which $R_1$ is hydroxy; and (iv) if desired, converting the said glycoside of formula I or II in which $R_1$ is hydroxy into a pharmaceutically acceptable salt thereof.

The novel amino sugars of formula III may be prepared by a process comprising:

(a) reacting methyl-2,3,6-trideoxy-α-L-glycerohexopyranoside 4-ulose of formula V:

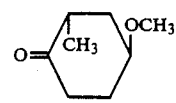

with hydroxylamine or an acid addition salt thereof to give a mixture of syn and anti oximes of formula VII:

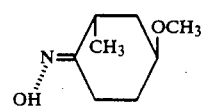

(b) hydrogenating the said mixture, protecting with a trifluoroacetyl group the amino group thus formed and separating the individual 4-N-trifluoroacetylated epimers of formulae VIIIe and VIIIf thus prepared:

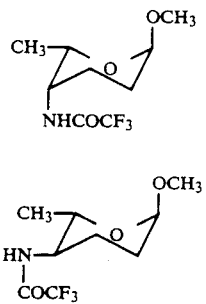
VIIIe

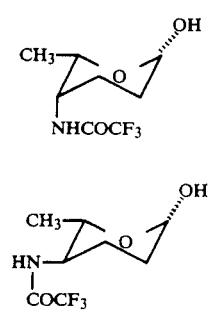
VIIIf (c) converting each epimer to the corresponding 1-hydroxy derivative of formula IXe or IXf:

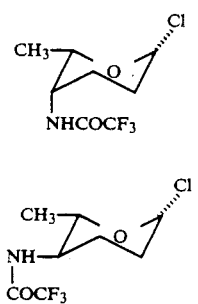
IXe

IXf and (d) converting each said 1-hydroxy derivative into the corresponding 1-chloro derivative IIIe or IIIf:

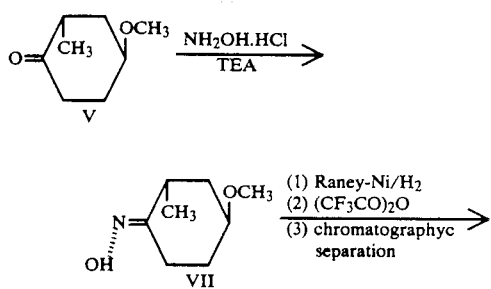
IIIe

IIIf

The preparation of the amino sugars of formula III is outlined in Scheme 1.

SCHEME I

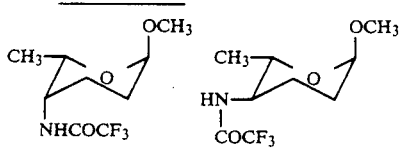

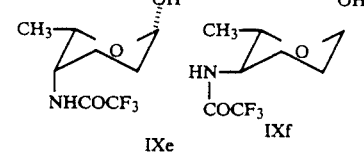

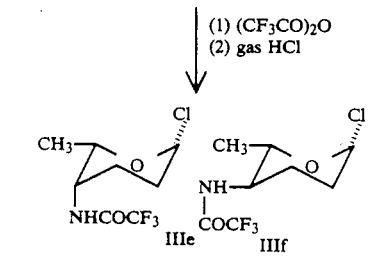

In step (a), treatment of methyl-2,3,6-trideoxy-α-L-glycerohexopyranoside-4-ulose (V) (see: J. S. Brimacombe et al. J. C. S. Perkin I, 1980, 273) may be with hydroxylamine hydrochloride in triethylamine (TEA) to give the syn and anti oximes VII.

Reduction of these in step (b) may be carried out by hydrogenation in anhydrous methanol and in the presence of Raney-Nickel, for example at 10 atmospheres for there hours. The hydrogenated mixture may be reacted with trifluoroacetic anhydride to obtain a mixture of N-trifluoroacetylated derivatives which, following chromatographic separation on a silica gel column, gives separately the corresponding trifluoroacetamido derivatives VIIIe and VIIIf. The eluent system may be methylene dichloride-acetone (95:5 v/v).

To convert each epimer to the corresponding 1-hydroxy derivative in step (c), each epimer VIIIe or VIIIf can be heated with acetic acid. Heating may be at 100° C. for one hour with 20% acetic acid. Step (d) can be effected by treatment with trifluoroacetic anhydride and HCl. For example, a 1-hydroxy epimer may first be treated overnight at 0° C. with trifluoroacetic anhydride and subsequently, dissolved in diethyl ether, reacted overnight with gaseous HCl to give 2,3,4,6-tetradeoxy-3-trifluoroacetamido-L-threo-hexopyranosyl chloride (IIIe) and 2,3,4,6-tetradeoxy-3-trifluoroacetamido-L-erythro-hexopyranosyl chloride (IIIf).

The preparation of the daunorubicin and doxorubicin derivatives of formulae I and II is illustrated by the following reaction Scheme II:

SCHEME II

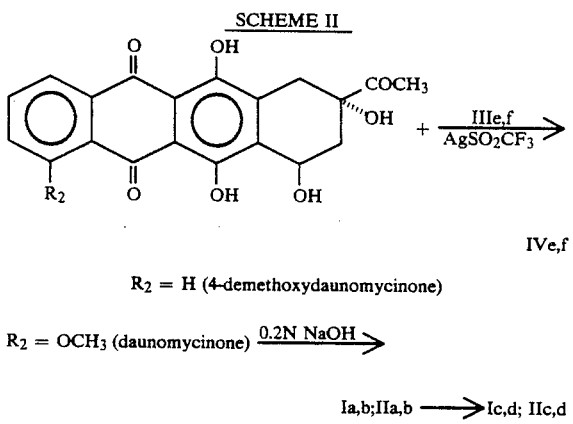

$R_2$ = H (4-demethoxydaunomycinone)

$R_2$ = OCH$_3$ (daunomycinone) $\xrightarrow{0.2N\ NaOH}$

Ia,b;IIa,b $\longrightarrow$ Ic,d; IIc,d

In Scheme II, 4-demethoxydaunomycinone ($R_2$=H) or daunomycinone ($R_2$=OCH$_3$) is condensed with a compound of formula IIIe or f in the presence of silver trifluoromethanesulphonate to form the N-trifluoroacetyl glycoside IVe or f from which compounds of formula Ia,b, or IIa,b are obtained by removing the amino protecting group by mild alkaline hydrolysis.

The conditions under which the condensation may be carried out are those described in U.S. Pat. No. 4,112,074. The compounds Ia,b and IIa,b may be converted respectively to Ic,d and IIc,d ($R_1$=OH) by bromination at the 14-position and by hydrolysis of the 14-bromo derivative with aqueous sodium formate. The bromination and hydrolysis conditions are typically those described in U.S. Pat. No. 4,122,076 or GB-A-1217133.

According to an embodiment of this process 4-demethoxydaunomycinone, dissolved in dry methylene chloride, is reacted at room temperature and for 1 hour with 1-chloro-2,3,4,6-tetradeoxy-4-(N-trifluoroacetamideo)-L-threo-hexopyranoside (IIIe) in presence of molecular sieves and silver trifluoromethanesulphonate to obtain a N-protected glycoside IVe ($R_2$=H, X=H, Y=NH-COCF$_3$) which, dissolved in acetone, is submitted at a temperature of 0° C. and for 1 hour, to a mild alkaline hydrolysis with 0.2N aqueous sodium hydroxide to give the compound of formula Ia as a free base which, by treatment with methanolic hydrogen chloride is isolated as its hydrochloride.

If desired, Ia is reacted with bromine in chloroform to obtain its 14-bromo derivative from which, after hydrolysis at room temperature and for 48 hours under nitrogen with an aqueous solution of sodium formate, the compound of formula Ic is obtained as a free base and, by treatment with anhydrous methanolic hydrogen chloride, is isolated as its hydrochloride.

Compounds IIa and IIc may be obtained in like fashion, starting from 1-chloro-2,3,4,6-tetradeoxy-4-(N-trifluoroacetamido)-L-erythro-hexapyranoside (IIIf). Starting from daunomycinone, compounds Ib, Id, IIb and IId can be obtained instead.

The present invention also provides a pharmaceutical composition comprising as active ingredient an anthracycline glycoside of formula I or II or a pharmaceutically acceptable salt thereof together with a pharmaceutically acceptable carrier or diluent. A therapeutically effective amount of a compound of the invention is combined with an inert carrier. Conventional carriers may be used and the compositions may be formulated in conventional manner.

The compounds of the invention are useful in methods of treatment of the human or animal body by therapy. In particular the compounds of the invention are useful as antitumor agents by administering a therapeutically effective amount of the compound to a patient.

The following Examples illustrate the invention.

EXAMPLE 1

Preparation of methyl-2,3,4,6-tetradeoxy-4-trifluoroacetamido-α-L-threo-hexopyranoside (VIIIe) and methyl-2,3,4,6-tetradeoxy-4-trifluoroacetamido-α-L-erythro-hexopyranoside (VIIIf)

1 g of methyl-2,3,6-trideoxy-α-L-glycero-hexopyranoside-4-ulose (V) (6.94 mmol), was added to a solution of 2.4 g of hydroxylamine hydrochloride in 50 ml of methanol and 4.8 ml of triethylamine. The reaction mixture was stirred at room temperature for one hour, then diluted with 150 ml of methylene dichloride and 100 ml of water.

The organic phase was evaporated off, washed with water and concentrated under vacuum to give a mixture of syn and anti oximes VII in the form of syrup.

The syrup was dissolved in 100 ml of dry methanol and hydrogenated in the presence of Raney Nikel at 10 atmosphere for three hours.

The filtred solution was evaporated under reduced pressure and the residue was treated with 6 ml of trifluoroacetic anhydride in 50 ml of methylene dichloride to give, after chromatographic separation on a silica-gel column eluting with methylene dichloride and 5% acetone, 0.63 g (yield 42%) of compound VIIIe and 0.57 g (yield 38%) of compound VIIIf. The structure of these compounds were assigned on the basis of PMR studies (200 MHz, CDCl$_3$, δ)

PMR spectrum of compound VIIIe: 1.18 (d,J=6.5 Hz, 3H, C$\underline{H}$$_3$-5); 1.7–1.9 (m, 4H, C$\underline{H}$$_2$-2, C$\underline{H}$$_2$-3) 3.42 (s, OC$\underline{H}$$_3$); 4.05 (m, 1H, H-4); 4.35 (dq, J=1.0, 6.5 Hz, 1H, $\underline{H}$-5); 5.08 (m, 1H, $\underline{H}$-1); 6.65 (bd, J=9.0 Hz, 1H, $\underline{NH}$—CO).

PMR spectrum of compound VIIIf: 1.20 (d, J=6.0 Hz, 3H, C$\underline{H}$$_3$-5); 1.5–2.0 (m, 4H, C$\underline{H}$$_2$-2, C$\underline{H}$$_2$-3) 3.38 (s, OC$\underline{H}$$_3$); 4.07 (m, 2H, H-4, H-5); 4.89 (m, 1$\underline{H}$, $\underline{H}$-1); 7.26 (bd, J=8.0 Hz, 1H, $\underline{NH}$—CO).

EXAMPLE 2

Preparation of 2,3,4,6-tetradeoxy-3-trifluoroacetamido-L-threo-hexopyranosyl-chloride (IIIe)

A solution of 0.46 g (2 mmol) of compound VIIIe, prepared as described in Example 1, dissolved in 40 ml of acetic acid and 160 ml of water, was heated for one hour at 100° C.

The reaction mixture was evaporated under reduced pressure to give 2,3,4,6-tetradeoxy-4-trifluoroacetamido-L-threo-hexose (IXe) in the form of syrup, which was dissolved in 20 ml of methylene dichloride and treated at 0° C. with 4 ml of trifluoroacetic anhydride.

After one night at 0° C., the reaction mixture was evaporated and the residue, dissolved in 20 ml of anhydrous diethyl ether, was satured at 0° C. with hydrogen chloride.

After standing at 0° C. overnight, the reaction mixture was evaporated in vacuum to give the title compound suitable for the coupling reaction without further purification.

EXAMPLE 3

Preparation of 2,3,4,6-tetradeoxy-4-trifluoroacetamido-L-erythro-hexo-pyranosyl chloride (IIIf)

Starting from methyl-2,3,4,6-tetradeoxy-4-trifluoroacetamido-α-L-erythro-hexopyranoside (VIIIf), prepared as described in Example 1, the title compound was prepared following the procedure described in Example 2.

EXAMPLE 4

Preparation of 4-demethoxy-3'-deamino-4'-deoxy-4'-aminodaunorubicin (Ia)

The condensation of 4-demethoxydaunomycinone (0.48 g, 1 mmol) dissolved in 70 ml of dry methylene dichloride with 2,3,4,6-tetradeoxy-3-trifluoroacetamido-L-threo-hexopyranosyl chloride (IIIe) (0.37 g, 1.5 mmol), in the presence of molecular sieves (4A), was performed using silver trifluoromethanesulfonate (0.38 g in 10 ml of diethyl ether) as catalyst.

After 30 minutes, under vigorous stirring at room temperature, the reaction mixture was treated with a satured aqueous solution of sodium hydrogen carbonate, and the organic phase was separated off and evaporated under reduced pressure to give, after chromatographic purification, 4-demethoxy-3'-deamino-4'-deoxy-4'-trifluoroacetamidodaunorubicin (IVe, $R_2$=H) 0.42 g, yield 70%, m.p. 178°–180° C. with decomposition.

PMR (200 MHz, CDCl$_3$, inter alia δ, 1.18 (d, J=6.5 Hz, 3H, $CH_3$-5'); 1.7–1.9 (m, 4H, $CH_2$-2', $CH_2$-3'); 2.14 (dd, J=4.0, 15.0 Hz, 1H, H-8ax); 2.32 (m, 1H, H-8eq); 2.42 (s, 3H, $COCH_3$); 2.98 (d, J=19.0 Hz, 1H, H-10ax); 3.24 (dd, J=1.0, 19.0 Hz, 1H, H-10e); 4.05 (m, 1H, H-4'); 4.35 (dq, J=1.0, 6.5 Hz, 1H, H-5'); 4.63 (s, 1H, OH-9); 5.28 (m, 1H, H-7); 5.44 (m, 1H, H-1'); 6.65 (bd, J=9.0 Hz, 1H, NH CO); 7.83 (m, 2H, H-1, H-4); 13.28 (s, 1H, OH-11); 13.58 (s, 1H, OH-6).

0.4 g of the N-trifluoroacetyl derivative was dissolved in 70 ml of 0.2N aqueous sodium hydroxide and stirred at room temperature. After one hour the reaction mixture was acidified to pH 3 with aqueous hydrochloric acid and then extracted with methylene dichloride. The aqueous phase, adjusted to pH 8.1, was extracted with methylene dichloride and the extract was washed with water, dried over annydrous sodium sulphate and concentrated to a small volume. Hydrogen chloride and diethyl ether was added to give the title compound Ia as hydrochloride; m.p. 155°–156° C. with decomposition.

EXAMPLE 5

Preparation of 3'-deamino-4'-deoxy-4'-aminodaunorubicin (Ib)

Starting from daunomycinone and 2,3,4,6-tetradeoxy-3-trifluoroacetamido-L-threo-hexopyranosyl chloride (IIIe), prepared as described in Example 2, the title compound was prepared following the procedure described in Example 4; m.p. 156°–157° C. with decomposition. PMR of the corresponding trifluoroacetamido derivative is reported.

PMR 200 MHz, CDCl$_3$, inter alia δ 1.16 (d, J=6.5 Hz, 3H, $CH_3$-5'); 1.5–2.0 (m, 4H, $CH_2$-2', $CH_2$-3'); 2.13 (dd, J=4.0, 15.0 Hz, 1H, H-8ax); 2.20 (ddd, J=2.0, 2.0, 15.0 Hz, H-8e); 2.41 (s, 3H, $COCH_3$); 2.96 (d, J=19.0 Hz, 1H, H-10ax); 3.24 (dd, J=2.0, 19.0 Hz, 1H, H-10e); 4.07 (m, 1H, H-4'); 4.08 (s, 3H, $OCH_3$); 4.34 (dq, J=1.0, 6.5 Hz, 1H, h-5'); 4.62 (s, 1H, OH-9); 5.31 (m, 1H, H-7); 5.46 (m, 1H, H -1'); 6.63 (bd, J=9.5 Hz, 1H, NHCO); 7.39 (d, J=8.5 Hz, 1H, H-3); 7.78 (t, J=8.5 Hz, 1H, H-2); 8.03 (q, J=8.5 Hz, 1H, H-1); 13.29 (s, 1H, OH-11); 14.01 (s, 1H, OH-6).

EXAMPLE 6

Preparation of 4-demethoxy-3'-deamino-4'-deoxy-4'-aminodoxorubicin (Ic)

0.2 g of 4-demethoxy-3'-deamino—4'-aminodaunorubicin (Ia) was dissolved in a mixture of anhydrous methanol and dioxane and added with a solution of 1 g of bromine in 10 ml of methylene dichloride, according to the procedure described in U.S. Pat. No. 4,122,076, to afford the 14-bromo derivative, which was precipitated by adding diethyl ether. The crude product was dissolved in little acetone and treated with 0.3 g of sodium formate dissolved in 1 ml of water. The reaction mixture was stirred at room temperature for 30 hours, then water was added and extracted with methylene dichloride. The aqueous phase was added with 5 ml of an 8% aqueous solution of hydrogen carbonate and repedeatedly extracted with methylene dichloride. The organic extracts were dried over anhydrous sodium sulphate, filtered off and evaporated to small volume under vacuum. The resulting red solution was adjusted to pH 3.5 with methanolic hydrogen chloride, then added with an excess of diethyl ether to give 0.16 g, yield 77%, of the title compound as hydrochloride.

m.p. 158°–159° C. with decomposition.

TLC on Kieselgel plates (Merck F$_{254}$) using the solvent system: methylene dichloride/methanol/acetic acid/water (80:20:7:3 by volume) Rf=0.52.

EXAMPLE 7

Preparation of 3'-deamino-4'-deoxy-4'-aminodoxorubicin (Id)

The chemical transformation of 3'-deamino-4'-deoxy-4'-aminodaunorubicin (Ib) to the title compound was achieved as described in Exampl 6(m.p. 148°–149° C. with decomposition).

TLC on Kieselgel plates (Merck F 254) using the solvent system: methylene dichloride/methanol/acetic acid/ water (80:20:7:3 by volume) Rf=0.48

EXAMPLE 8

Preparation of 4-demethoxy-3'-deamino-4'-deoxy-4'-epi-aminodaunorubicin (IIa)

The coupling of 4-demethoxydaunomycinone with 2,3,4,6-tetradeoxy-3-trifluoroacetamido-L-erythro-hexopyranosyl chloride (IIIf), was performed following the procedure described in Example 4

The PMR spectrum of the protected trifluoroacetamido derivative is reported:

PMR 200 MHz, CDCl$_3$, inter alia δ 1.20 (d, J=6.0 Hz, 3H, $CH_3$-5'); 1.5–2.0 (m, 4H, $CH_2$-2', $CH_2$-3'); 2.10 (dd, J=4.5, 15.0 Hz, 1H, H-8ax); 2.42 (s, 3H, $COCH_3$); 2.66 (ddd, J=2.0, 2.0, 15.0 Hz, 1H, H-8eq); 3.0 (d, J=19.0 Hz, 1H, H-10ax); 3.25 (dd, J=2.0, 19.0 Hz, 1H, H-10eq); 4.07 (m, 2H, H-4', H-5'); 4.09 (s, 1H, OH-9); 5.20 (dd, J=4.5, 2.0 Hz, 1H, H-7); 5.25 (d, J=3.5 Hz, 1H, H-1'); 7.26 (bd, J=8.0 Hz, 1H, NHCO); 7.85 (m, 2H, H-2, H-3); 8.36 (m, 2H, H-1, H-4).

EXAMPLE 9

Preparation of 3'-deamino-4'-deoxy-4'-epi-amino-daunorubicin (IIb)

Coupling of daunomycinone with 2,3,4,6-tetradeoxy-3-trifluoroacetamido-L-erythro-hexopyranosyl chloride (IIIf) following the procedure described in Example 4, gave the title compound as its hydrochloride; m.p. 183°–184° C. with decomposition. TLC on Kieselgel plates (Merck $F_{254}$) using the solvent system methylene dichloride/methanol/acetic acid/water (80:20:7:3 by volume) Rf=0.67

EXAMPLE 10

Preparation of 4-demethoxy-3'-deamino-4'-deoxy-4'-epi-aminodoxorubicin (IIc)

Chemical transformation of compound IIa, prepared as described in Example 8, was performed by 14-bromination followed by hydrolysis according to the procedure described in Example 6.

TLC on Kieselgel plates (Merck $F_{254}$) using the solvent system:methylene dichloride/methanol/acetic acid/water (80:20:7:3 by volume) Rf=0.53

EXAMPLE 11

Preparation of 3'-deamino-4'-deoxy-4'-epi-aminodoxorubicin (IId)

The title compound was obtained from compound IIb following the procedure described in Example 6.

TLC on Kieselgel plates (Merck $F_{254}$) using the solvent system:methylene dichloride/methanol/acetic acid/water (80:20:7:3 by volume) Rf=0.50.

Biological activity of Compounds Ia, Ib, Id, IIa, IIc

The antileukemic activity of Ia and IIa, in comparison with DXR (doxorubicin) and DNR (daunorubicin), was tested against murine P388 and Gross Leukemias.

Against P388 leukemia both derivatives showed a comparable antitumor activity than DXR and DNR. On Gross leukemia all tested were found active, as were DXR and DNR, on increase of the survival time of mice; IIa and IIc were the most potent compounds.

Compounds Ia and IIa were also evaluated against different human and solid tumors; the results are summarized in Tables 4–8. Compound IIa was more potent and active than Ia against all solid tumors tested. Against tumor DXR-resistent (LoVo/DXR, MTV/DXR and A549) compound IIa showed a similar antitumor effect than that of DXR.

On LoVo tumor, compound IIa showed the same activity than LoVo/DXR, whereas compound Ia was completly inactive. On Lewis lung ca.model, sensitive to DXR, compound IIa was active, as DXR, on tumor growth inhibition and less active against the survival time of mice; compound Ia was inactive on both parameters.

The compounds were tested by dissolving them, as hydrochlorides, in water.

The in vitro cytotoxicity is reported in Table 1.

TABLE 1

Cytotoxic activity of Compounds.

| Compounds | $ID_{50}$ (μ/ml) | |
|---|---|---|
| | LoVo | LoVo/DXR |
| DNR | 50.3 | 1805 |
| DXR | 54.7 | 2105 |
| Ib | 117.5 | 330 |
| Ia | 31.5 | 43.5 |
| IIa | 10.3 | 9.5 |
| Id | 50.3 | 346 |
| IIc | 1.5 | 8.2 |

TABLE 2

Effect against P388 ascitic leukemia[a]

| Compound | optimal dose[b] mg/Kg | T/C %[c] | Toxic[d] death |
|---|---|---|---|
| DNR | 22.5 | 222 | 0/10 |
| DXR | 16.9 | 225 | 0/10 |
| Ia | 19.5 | 200 | 0/10 |
| IIa | 4 | 225 | 0/10 |

[a]Experiments were performed in $CDF_1$ mice, inoculated i.v. with $10^6$ leukemia cells
[b]Single i.v. dose on day 1 after tumor inoculum.
[c] Median survival time of treated mice/median survival time of control × 100.
[d]Evaluated on the basis of autoptic findings.

TABLE 3

Effect against murine Gross leukemia[a]

| Compound | optimal dose[b] mg/Kg | T/C %[c] | Toxic[d] death |
|---|---|---|---|
| DNR | 15 | 200 | 0/10 |
| DXR | 13-16.9 | 200-250 | 0/10 |
| Ib | 65 | 240 | 0/10 |
| Ia | 12.5 | 240 | 0/10 |
| IIa | 4 | 160 | 0/10 |
| Id | 6.7 | 200 | 0/10 |
| IIc | 1 | 217 | 0/10 |

[a]Experiments were performed in C3H/He mice, inoculated i.v. with $2 \times 10^6$ leukemia cells
[b]Single i.v. dose on day 1 after tumor inoculum.
[c]Median survival time of treated mice/median survival time of control × 100.
[3]Evaluated on the basis of autoptic findings.

TABLE 4

Effect against Human Colon ca. (LoVo/DXR)[a]

| Compound | optimal dose[b] mg/Kg | tumor inhibition[c] % |
|---|---|---|
| DXR | 6 | 30 |
| Ia | 7.5 | 13 |
| IIa | 4 | 41 |

[a]experiment was performed in Swiss-nude mice, transplanted s.c. with tumor fragments
[b]treatment i.v. was carried out once a week for three weeks, starting when the tumor was palpable
[c]percentage of tumor growth inhibition in respect to control was calculated 1 week after the last treatment

TABLE 5

Effect against Murine Mammary ca. (MTV/DXR)[a]

| Compound | optimal dose[b] mg/Kg | T/C[c] % | tumor inhibition % |
|---|---|---|---|
| DXR | 6 | 84 | 52 |
| IIa | 5 | 146 | 44 |

[a]experiment was carried out in C3H/He mice, transplanted s.c. with tumor fragments
[b]treatment i.v. was carried out once a week for three weeks, starting when the tumor was palpable
[c]percentage of tumor growth inhibition in respect to control was calculated 1 week after the last treatment

TABLE 6

Effect against Human Colon adenocarcinoma (LoVo)[a]

| Compound | optimal dose[b] mg/Kg | tumor inhibition[c] % |
|---|---|---|
| DNR | 8 tox | 54 |
| DXR | 6 | 62 |
| Ia | 7.5 | 11 |
| IIa | 4–5 | 54–56 |

[a]experiment was performed in Swiss-nude mice, transplanted s.c. with tumor fragments

[b]treatment i.v. was carried out once a week for three weeks, starting when the tumor was palpable

[c]percentage of tumor growth inhibition in respect to control was calculated 1 week after the last treatment

TABLE 7

Effect against human lung adenocarcinoma (A549)[a]

| Compound | optimal dose[b] mg/Kg | tumor inhibition[c] % |
|---|---|---|
| DXR | 6 | 44 |
| Ia | 9 | 13 |
| IIa | 5 | 49 |

[a]experiment was performed in Swiss-nude mice, transplanted s.c. with tumor fragments

[b]treatment i.v. was carried out once a week for three weeks, starting when the tumor was palpable

[c]percentage of tumor growth inhibition in respect to control was calculated 1 week after the last treatment

TABLE 8

Effect against Lewis Lung ca.[a]

| Compound | optimal dose[b] mg/Kg | tumor inhibition[c] % | T/C[d] % |
|---|---|---|---|
| DXR | 6–7.5 | 85–95 | 148–169 |
| DNR | 8 | 47 | 135 |
| Ia | 7.5 | 7 | 104 |
| IIa | 4 | 84 | 122 |

[a]experiment was performed in C57 B1/6 mice, inoculated i.v. with 10[5] tumor cells.

[b]treatment i.v. was carried out once a week for three weeks, starting on day 1 after tumor transplant

[c]percentage of tumor growth inhibition in respect to control was calculated 1 week after the last treatment

[d]median survival time of treated mice/median survival time of control × 100

We claim:

1. An anthracycline glycoside of the formula I or II:

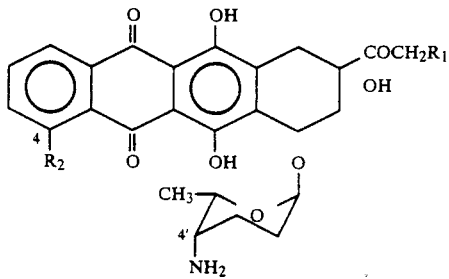

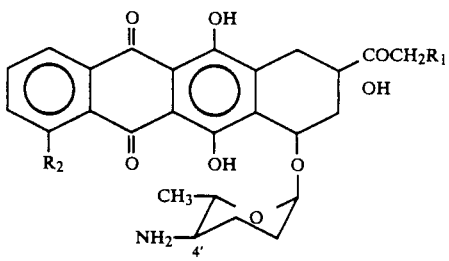

wherein $R_1$ is hydrogen or a hydroxy group and $R_2$ is hydrogen or a methoxy group; and their pharmaceutically acceptable acid addition salts.

2. A compound according to claim 1, which is 4-demethoxy-3'-deamino-4'-deoxy-4'-aminodaunorubicin or its hydrochloride.

3. A compound according to claim 1, which is 3'-deamino-4'-deoxy-4'-aminodaunorubicin or its hydrochloride.

4. A compound according to claim 1, which is 4-demethoxy-3'-deamino-4'-deoxy-4'-aminodoxorubicin or its hydrochloride.

5. A compound according to claim 1, which is 3'-deamino-4'-deoxy-4'-aminodoxorubicin or its hydrochloride.

6. A compound according to claim 1, which is 4-demethoxy-3'-deamino-4'-deoxy-4'-epi-aminodaunorubicin or its hydrochloride.

7. A compound according to claim 1, which is 3'-deamino-4'-deoxy-4'-epi-aminodaunorubicin or its hydrochloride.

8. A compound according to claim 1, which is 4-demethoxy-3'-deamino-4'-deoxy-4'-epi-aminodoxorubicin or its hydrochloride.

9. A compound according to claim 1, which is 3'-deamino-4'-deoxy-4'-epi-aminodoxorubicin or its hydrochloride.

10. A pharmaceutical composition comprising a pharmaceutically effective amount of an anthracycline glycoside of formula I or II as defined in claim 1 or a pharmaceutically acceptable salt thereof in admixture with a pharmaceutically acceptable diluent or carrier.

* * * * *